United States Patent [19]
Nagase

[11] Patent Number: 5,326,373
[45] Date of Patent: Jul. 5, 1994

[54] TUBULAR CONNECTOR
[75] Inventor: Toshio Nagase, Tsukuba, Japan
[73] Assignee: Nippon Zeon Co., Ltd., Tokyo, Japan
[21] Appl. No.: 711,789
[22] Filed: Jun. 7, 1991

Related U.S. Application Data
[60] Division of Ser. No. 517,461, May 4, 1990, Pat. No. 5,041,131, which is a continuation of Ser. No. 185,356, Apr. 18, 1988, abandoned, which is a continuation of Ser. No. 899,846, Aug. 25, 1986, abandoned.

[30] Foreign Application Priority Data
Aug. 30, 1985 [JP] Japan .................... 60-133310

[51] Int. Cl.$^5$ .............................. A61M 1/10
[52] U.S. Cl. ................................... 623/3; 623/1; 623/2
[58] Field of Search .................... 623/1-3, 623/11, 12; 604/277; 137/515, 515.3, 515.7; 251/305, 306

[56] References Cited
U.S. PATENT DOCUMENTS

| | | | |
|---|---|---|---|
| 1,824,168 | 9/1931 | Orton . | |
| 2,294,568 | 9/1941 | Neilsen . | |
| 2,900,998 | 8/1959 | Lortz . | |
| 3,409,913 | 11/1968 | Kantrowitz | 623/3 |
| 3,409,914 | 11/1968 | Jones | 623/3 X |
| 3,636,570 | 1/1972 | Nielson | 623/3 |
| 3,696,674 | 10/1972 | Spencer . | |
| 4,086,665 | 5/1978 | Poirier | 623/3 X |
| 4,118,806 | 10/1978 | Poierer et al. | 623/3 X |
| 4,211,325 | 7/1980 | Wright | 623/2 X |
| 4,221,360 | 9/1980 | Yasuoka et al. . | |
| 4,223,430 | 9/1980 | Sherlaw . | |
| 4,387,879 | 6/1983 | Tauschinski . | |
| 4,397,049 | 8/1983 | Robinson et al. . | |
| 4,434,811 | 3/1984 | Murdoch . | |
| 4,605,041 | 8/1986 | Teumer . | |
| 4,626,243 | 12/1986 | Singh et al. | 604/141 |
| 4,650,486 | 3/1987 | Chareire | 623/3 |
| 4,721,109 | 1/1988 | Healey | 623/12 X |
| 4,753,236 | 6/1988 | Healey | 623/12 X |
| 4,769,032 | 9/1988 | Steinberg . | |
| 4,981,484 | 1/1991 | Holfert et al. | 623/3 |
| 5,041,131 | 8/1991 | Nagase | 623/3 |

Primary Examiner—Randall L. Green
Assistant Examiner—Elizabeth M. Burke
Attorney, Agent, or Firm—Nikaido, Marmelstein, Murray & Oram

[57] ABSTRACT
There is provided a tubular connector to connect first and second fluid tubes wherein separately formed first and second tubular sections are jointed together with a built-in artificial valve in the inside fluid path.

5 Claims, 10 Drawing Sheets

TUBULAR CONNECTOR

This is a division of originally filed application Ser. No. 899,846, filed on Aug. 25, 1986, continued on Apr. 18, 1988 as application Ser. No. 185,356, and continued on May 4, 1990 as application Ser. No. 517,461 now U.S. Pat. No. 5,041,131.

BACKGROUND OF THE INVENTION

1. Field of the Invention

The present invention relates to a tubular connector used to connect first and second fluid tubes, for example, one suitably applicable to a blood pumping device for an artificial heart.

2. Description of the Prior Art

In recent years, increasing effort has been expended in the development of artificial heart devices including those used paracorporeally in heart and other operations to assist and temporarily substitute the heart in its function. For example, as illustrated in FIG. 1, a pair of units of sac type blood pumping devices 11 are connected, one between the right atrium of heart 10 and pulmonary artery and the other between the left atrium and aorta. Also in Japan, one of the leading countries in this field of technology, such a blood pumping device has been studied, and is already clinically applied as the temporary assist heart.

As explicitly illustrated in FIG. 2, this sac type blood pumping device 11 is composed of two major components, a pressure resistant housing outer case 1, for example, made of polycarbonate or polyurethane resin and a flat sac 2 that is housed airtight inside the above housing outer case to provide a blood chamber. On top of this flat sac 2, a blood inlet port 3 and a blood outlet port 4 are formed, rising upward almost in parallel to each other, to provide passages to and from the inside space of blood chamber. A flange 5 is provided around the circumference of the top of sac 2 to form part of the housing. This flange airtightly closes the sac 2 in the housing outer case 1. Further, as illustrated in FIGS. 3 and 4, the blood inlet port 3 and blood outlet port 4 are fitted inside with artificial check valves 6 and 7, respectively, on individual annular valve seats 20 so that the backflow of blood 17 may be prevented. Under the operation of these valves, blood 17 is introduced through the blood inlet port 3 into the sac 2 and pumped out pulsatively through the blood outlet port 4. For such pulsatile pumping of blood, a fluid, for example, air is alternately introduced from a compressed air source and sucked out under vacuumed pressure through a single port 8 provided at the bottom of housing outer case 1 so that as the outer pressure of sac 2 changes, the sac may swell and contract repeatedly. Cannulae 12, from a heart or a blood vessel, are connected to one side of individual connectors 13 while blood inlet ports 3 and blood outlet ports 4 on sacs 2 are connected to the other side thereof by fitting these cannulae and ports to the connectors until they are stopped by annular flanges 14 provided halfway between both ends of the connectors.

With the blood pumping device 11 as mentioned above, since the check valves 6 and 7 are built in the blood inlet port 3 and blood outlet port 4, respectively, it is necessary to have a sufficient dimensional accuracy at the built-in position of the valves. Namely, the inside surface of the blood inlet and outlet ports 3 and 4 must be finished to dimensions accurate enough for individual valve seats 20 for valves 6 and 7 to sit tight inside (on an annular swelling). For this end, molding requires an accurate core mold. Further, the construction, that the ports 3 and 4 to be fitted with a built-in valve are integrally formed with the sac 2 to be housed inside the pumping device 11, is very difficult to mold by a single step process because of the shape of the sac. This means multiple molding steps and therefore very often means a higher molding cost.

It is noted that since the connectors 13 as mentioned above are shaped as shown and are rigid, it will be very difficult to alleviate the above problem by building the valves 6 or 7 in the connectors.

OBJECTS AND SUMMARY OF THE INVENTION

Accordingly, an object of the invention is to provide a tubular connector that has a wider allowance on the dimensional accuracy at the installation point of an artificial valve to allow for easier installation of the valve.

Another object of the invention is to provide a tubular connector that not only has a wider allowance on dimensional accuracy at the installation point of an artificial valve but also allows installation of an artificial valve of various shapes and sizes with fewer formation steps and fewer gaps.

Another object of the invention is to provide a tubular connector of comparatively simple construction that is easy to produce, which is capable of accommodating an artificial valve satisfactorily, and which further allows measurements of the flow rate of a fluid.

Namely, the invention is concerned with a tubular connector capable of connecting first and second fluid tubes to each other wherein separate first and second tubular sections of the tubular connector are jointed together and an artificial valve is built in the inside fluid path.

Other objects, features and advantages of the invention will appear more fully from the following detailed description thereof.

DESCRIPTION OF THE PREFERRED EMBODIMENTS

Figure 1:
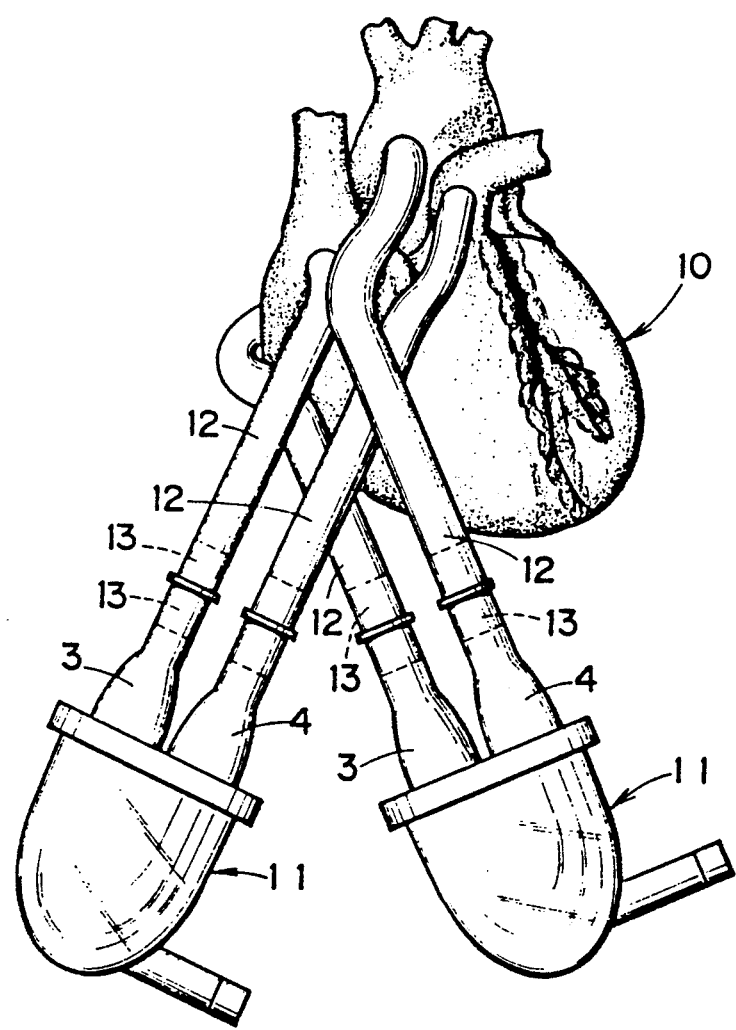
FIG. 1 is a schematic illustration of a blood pumping device of the prior art in the practically used condition thereof.
Figure 2:
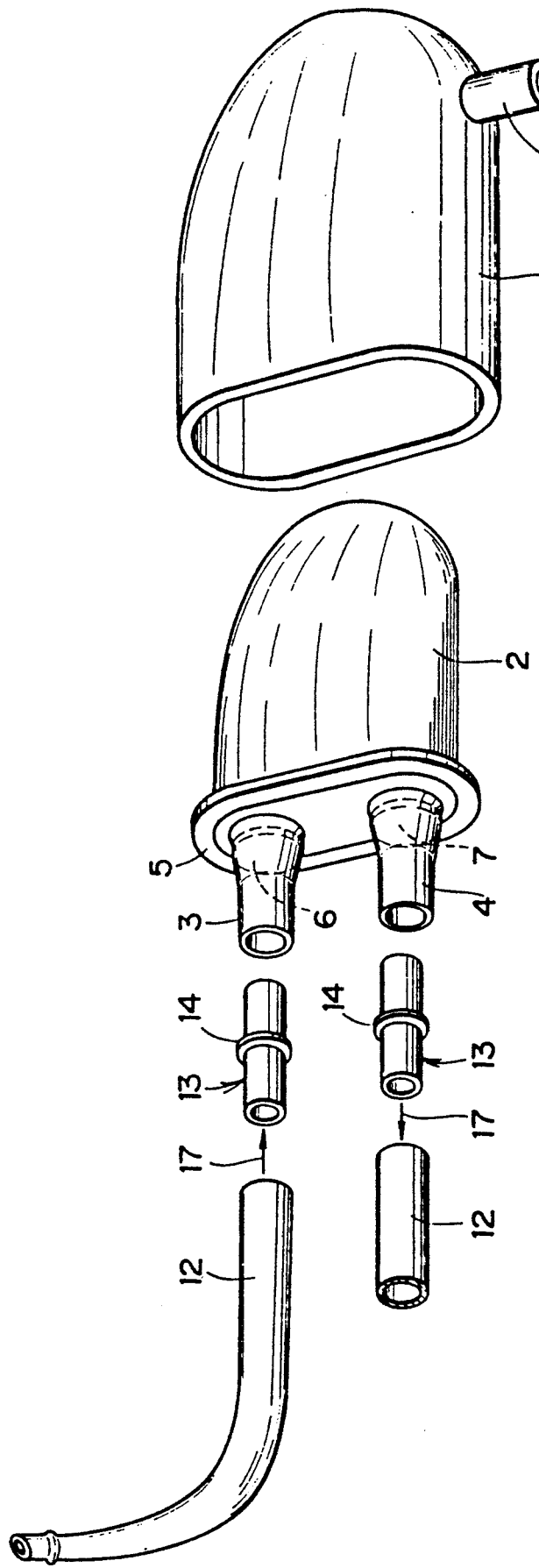
FIG. 2 is a perspective view of parts of the same blood pumping device.
Figure 3:
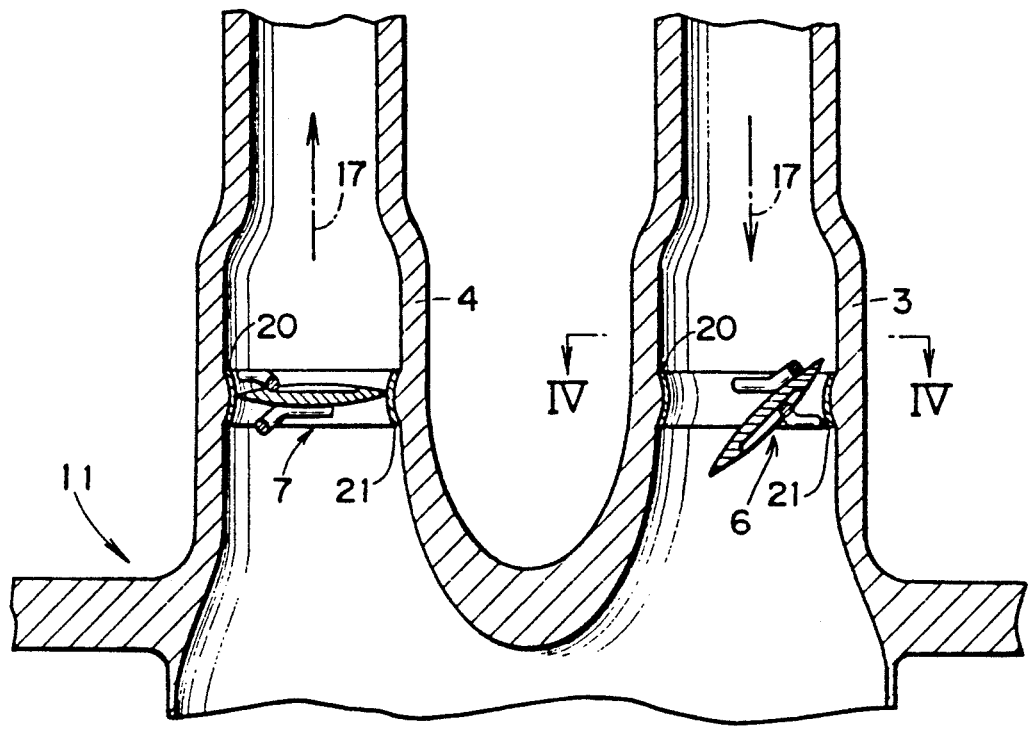
FIG. 3 is a cross-sectional view of the same blood pumping device at a level where an artificial valve is fixed.
Figure 4:
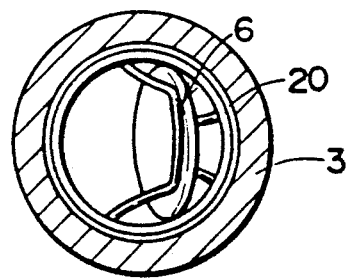
FIG. 4 is a cross-sectional view taken on line IV—IV in FIG. 3.
Figure 5:
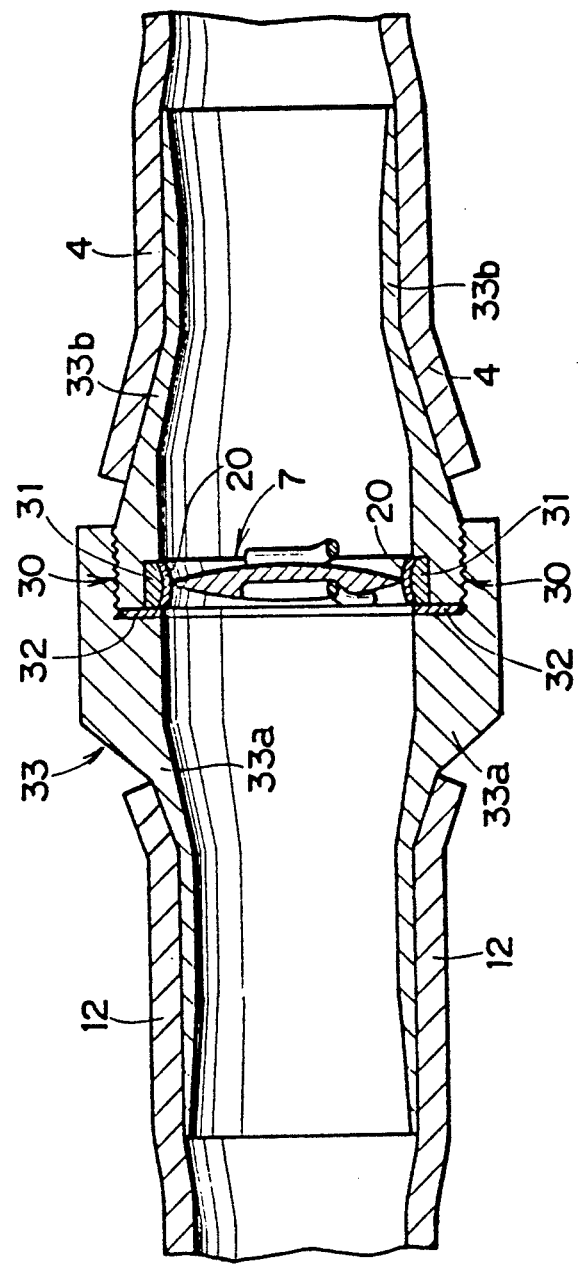
FIG. 5 is a cross-sectional view of a connector of the invention for a blood pumping device.
Figure 6:
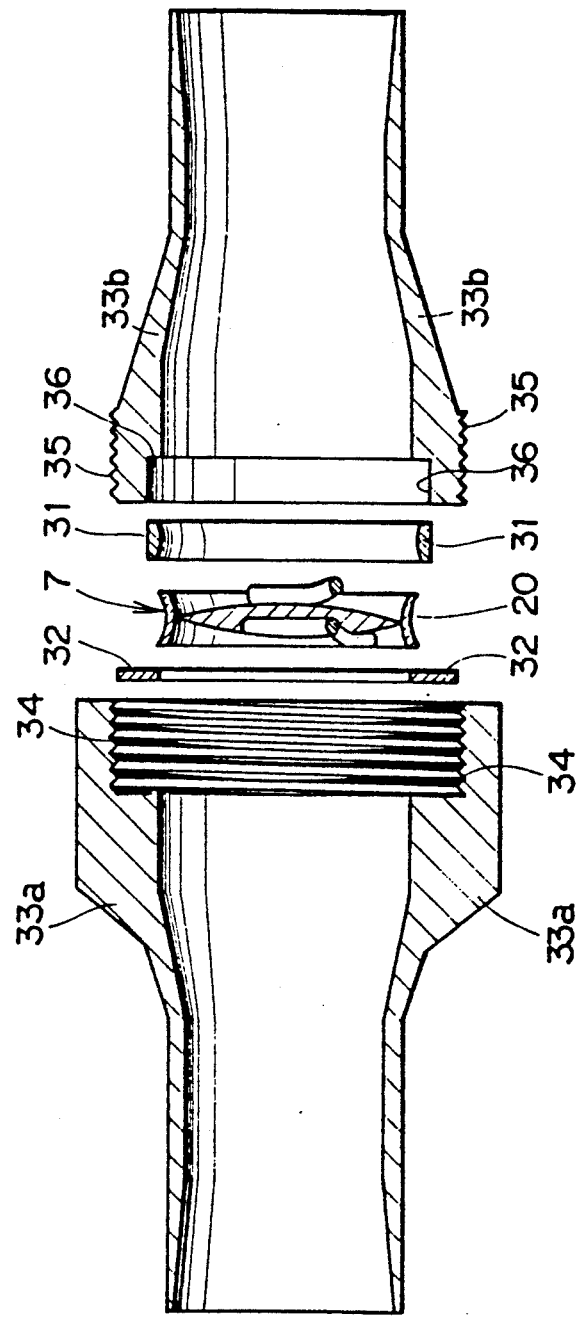
FIG. 6 is an exploded cross-sectional view of the same connector.

Quite different from the blood pumping device of the prior art as illustrated in FIGS. 1 to 3, a blood pumping device that uses tubular connectors as illustrated in FIGS. 5 and 6 (in these and all subsequent drawings and sometimes also in the following description, only the blood outlet side is explicitly illustrated and described and the blood inlet side is omitted since both sides are constructed similarly) has such a construction that the artificial valves 6 and 7 are not installed in the blood inlet port 3 and blood outlet port 4 of pumping device but built in, inside the tubular connectors 33 connecting these blood ports to cannulae connected to the heart or a blood vessel at the other ends. The connector 33 is not just designed to accommodate a built-in artificial valve 7 with valve seat 20 but has a specially devised mounting construction for such a valve. Namely, this connector 33 comprises a pair of tubular sections 33a and 33b, the former on the side of cannula 12 and the latter on the side of blood port 4, that are detachably screwed to each other through a threaded portion 30. Particularly, in the opening of the tubular section 33b on the side facing the tubular section 33a, an artificial valve 7 is fixed with insertion of a sealing ring (or resilient mount) 31 therebetween. It is noted that a packing 32 in the drawings is used to tightly joint the two tubular sections 33a and 33b.

The check valves 6 and 7 (or prosphesis valves) used above may be valves of known construction or commercially available valves. Examples are valves of ball type, disc type, leaflet type, etc. In the above ports 3 and 4, cannulae 12 and sac 2, parts that are brought in contact to blood may be made of an elastic polymer, preferably, plasticized polyvinyl chloride or polyurethane. In case of plasticized polyvinyl chloride, the so-called "polyvinyl chloride paste" composed of polyvinyl chloride powder and a plasticizer may be used for plasti-sol molding. On the other hand, the housing outer case 1 is made of rigid polyvinyl chloride, polycarbonate, polysulfone, etc. since the case must satisfy requirements for mechanical strength and transparency.

As illustrated in FIG. 6, the connector 33 is so constructed that in female thread 34 formed on one tubular section 33a, male thread 35 which is formed on the other tubular section 33b, may be screwed for jointing to each other and these tubular sections may be detached from each other by turning opposite to the sense for screwing in. Before the two tubular sections are jointed, an annular packing 32 is fitted on the side of tubular section 33a and an artificial valve 7 is mounted on the side of tubular section 33b. This artificial valve 7 is fitted into a sealing ring 31 that is in turn fitted to an annular recess 36 made in the inner surface of tubular section 33b. As the tubular sections 33a and 33b are jointed at this state, the artificial valve is fastened in position inside the connector. The entire length of connector is preferably practically transparent and may be formed by injection molding of polycarbonate, polysulfone, epoxy resin, or the like. Alternatively, however, the connector may be made of a metal, such as aluminium, stainless steel or the like.

The connector 33 of the present example may be supplied with the tubular sections 33a and 33b joined beforehand or these tubular sections, after being connected to the cannula 12 and blood port 4, may be supplied as separate parts for connection to each other before the start of a surgical operation.

The above connector 33 with a built-in artificial valve 7 has a wider allowance on the dimensional accuracy as compared to the construction of a prior blood pumping device wherein artificial valves are individually built in the blood inlet and outlet ports. The connector can thus positively and reliably accommodate and fasten artificial valves of various shapes and sizes at a given position even if there are dimensional variations at individual points involved since these variations are absorbed. Further, an artificial valve 7 can be secured in the connector 33 just by inserting the valve in a tubular section 33b from one end thereof and screwing the two tubular sections to each other for jointing. The artificial valve is thus very easy to install, being always fastened at a given position. Beside, the artificial valve 7, even if there are variations in the size of the valve or dimensions of the fitted portion thereof, can always be positively and securely fastened inside the connector by selection of a sealing ring 31 and packing 32 that have proper resiliency and size.

After installation of the artificial valve 7, it is easy to treat and/or work the artificial valve supporting zone, for example, to line with an antithrombogenetic material, such as polyurethane or polyether polyurethane-polydimethylsiloxane block copolymer and further trim the inner surface of the connector both upstream and downstream of the artificial valve 7. By contrast, with the prior blood pumping device as illustrated in FIG. 2, the antithrombogenetic material can be applied inside the blood inlet and outlet ports only from one side thereof (namely, from the free end).

In addition to the excellent function and effect as mentioned above of the construction in which an artificial valve 7 (or 6) is fixed inside the connector 33, removal of the artificial valve from the pumping device itself widens the allowance on the internal dimensions of such a pumping device to ease molding thereof. It thus becomes possible to mold the blood inlet and outlet ports and sac simultaneously in short time. This can readily be achieved by use of parting molds.

As mentioned above, according to the above example, first and second tubular sections are detachably jointed to form a connector, so that the artificial valve to be built-in can be mounted beforehand near the jointed zone of both tubular sections. As a result, the artificial valve mounting area has a wider allowance on dimensional accuracy for easier installation of the valve. Further, the connector can be set up readily and fast. For example, detached tubular sections are connected to a cannulae and a blood pumping device beforehand so that these tubular sections may be jointed on site. This method has a remarkable merit that even if a connector that has a sharp edge at both ends is used to reduce thrombus formation there is no danger that such a sharp edge may injure the operator's hand or be damaged.

The blood pumping device of the present example can be produced in a simplified process of much higher productivity and used in combination with the prior cannula as it is since artificial valves are built in individual connectors.

Figure 7:
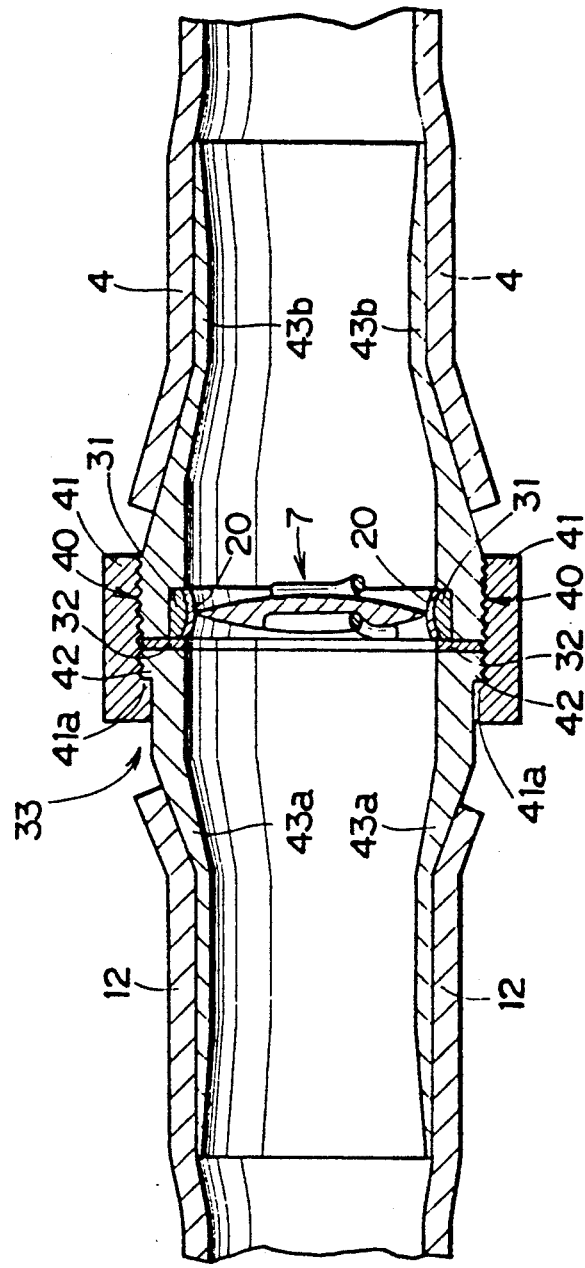
FIGS. 7, 8 and 9 are cross-sectional views of other connectors of the invention for the blood pumping device.
Figure 8:
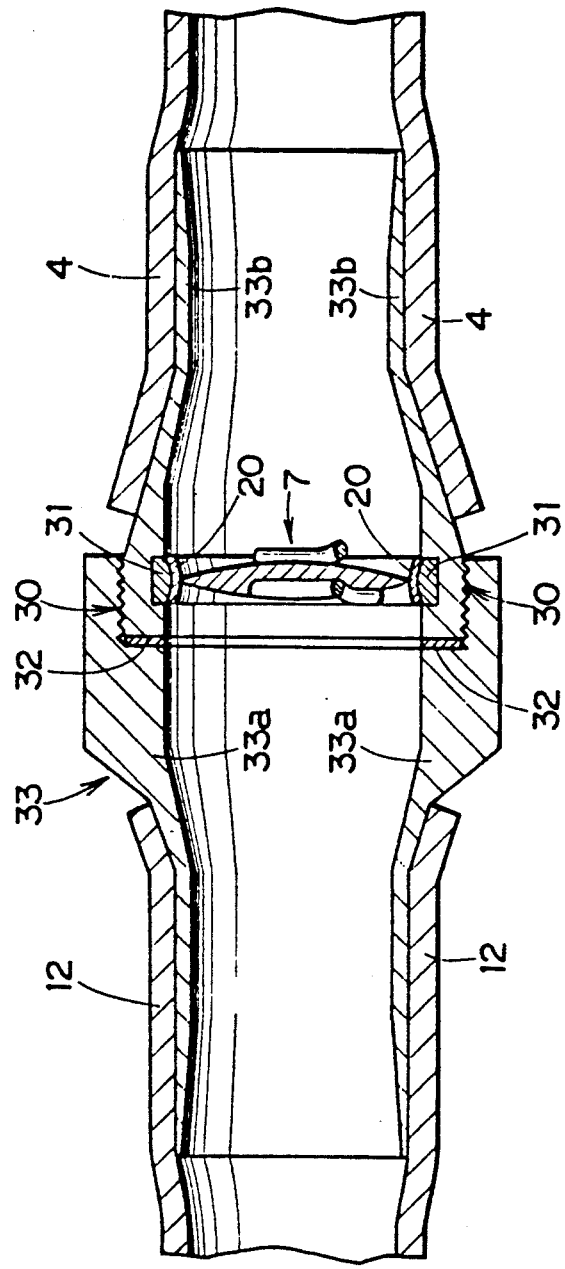

Another two examples of a connector also embodying the invention are illustrated in FIGS. 7 and 8. Portions that are common with the connector of FIGS. 5 and 6 are sometimes commonly numbered to omit the description.

The connector 33 of FIG. 7 adopts a so-called union joint as a means to detachably joint two tubular sections 43a and 43b wherein a union nut 41 is provided around the circumference of the jointed portion of both tubular sections. As at the threaded portion 30 as mentioned above, the union nut 41 and tubular section 43b mesh at a threaded portion 40 as the nut 41 is screwed toward the tubular section 43b until the rear end 41a of the former is stopped by a shoulder 42 of the tubular section 43a. The two tubular sections are thus firmly pressed against each other for tight jointing.

With such a union joint, the two tubular sections 43a and 43b can be jointed without revolving any of these tubular sections. Accordingly, the connector can be assembled with the port 4 (or port 3) and cannula 12 fitted in position beforehand and held in a stable condition.

Another example of a connector as illustrated in FIG. 8 differs from the example of FIG. 5 in that the artificial valve 7 is secured in the tubular section 33b slightly inward from the jointed end thereof. The artificial valve 7 can thus be secured more reliably in the tubular section 33b. With this setup, there is less danger that during connector assembly the artificial valve 7 and sealing ring 31 may come off to fall outside.

Figure 9:
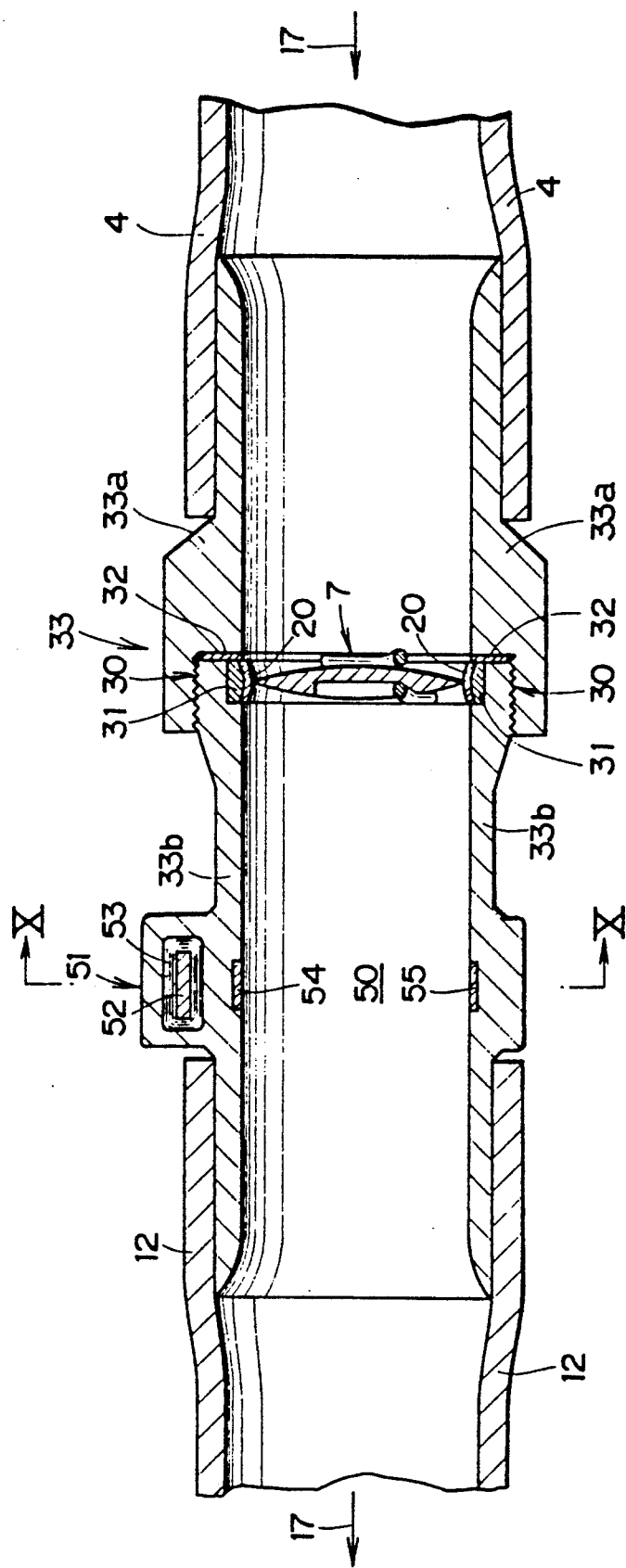
Figure 10:
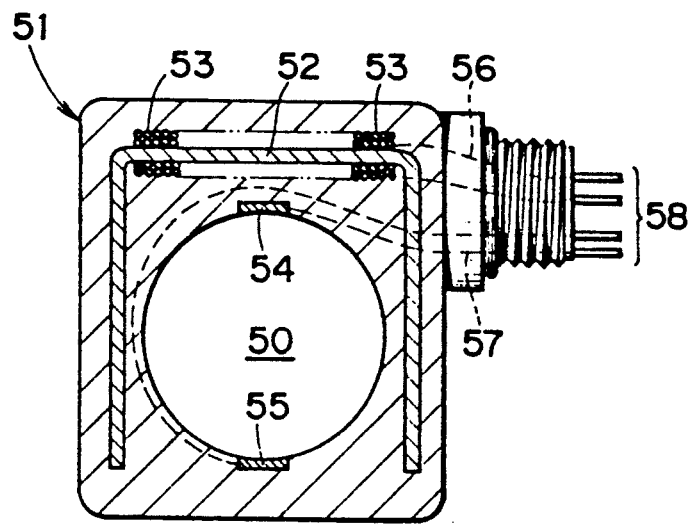
FIG. 10 is a cross-sectional view taken on line X—X in FIG. 9.

Another example of a connector for the blood pumping device as illustrated in FIGS. 9 and 10, like the foregoing examples of the invention, is constructed to accommodate a built-in artificial valve 7 inside the connector 33 composed of a pair of tubular sections 33a and 33b, the former on the side of blood port 4 and the latter on the side of cannula 12, detachably jointed by a threaded portion 30. Further, the main body of this connector (more specifically, the tubular section 33b) has a built-in probe 51 for an electromagnetic flowmeter around the blood path 50.

As already mentioned with reference to FIG. 6, the connector 33 is so constructed that in the female thread formed on one tubular section 33a, the male thread, which is formed on the other tubular section 33b, may be screwed for jointing to each other and these tubular sections may be detached from each other by revolving opposite to the sense for screwing in.

In this case, however, though the tubular section 33a can be molded by injection, the tubular section 33b is preferably formed by casting since this tubular section has a comparatively complicated construction, as illustrated in FIG. 10, because of the presence of built-in probe 51.

The probe 51 is composed of coils 53 wound on part of a U-shaped core 52 embedded in the body of tubular section 33b and a pair of opposing electrodes 54 and 55 disposed across the blood path 50. A pair of leads 56 from coils 53 and another pair of leads 57 from electrodes 54 and 55 are connected through individual terminals 58 to external circuits. Further, as illustrated, the probe is located downstream of the artificial valve 7, namely, at a position where blood flows in a steady flow. This means that the electromagnet can exert magnetic forces effectively. From this point of view, the probe 51 is preferably located distant enough from the artificial valve 7.

Beside the effects and functions as described with reference to the foregoing examples, the present example of a connector with both the artificial valve 7 (or 6) and probe 51 for the electromagnetic flowmeter built in can monitor the blood flow rate through electrodes 54 and 55 that are brought in direct contact to the blood flow, at a high accuracy in spite of a construction simple enough to get smooth blood flow that causes practically no thrombus formation.

Conventionally a connector and also a tube fitted with a probe (insertion tube type probe) are connected in series between the blood outlet port 4 and cannula 12. Such a double connector system is liable to cause thrombus formation at individual connections. By contrast, the present example uses just a single connector to effectively perform the above two functions, namely, prevention of blood backflow by an artificial valve and measurement of the blood flow rate, so that problems as mentioned above with the double connector system are alleviated almost fully.

It is noted that also in the present example the union joint as described with reference to FIG. 7 can be applied to joint the two tubular sections and the position of the artificial valve can be changed to conform to FIG. 8.

Figure 11:
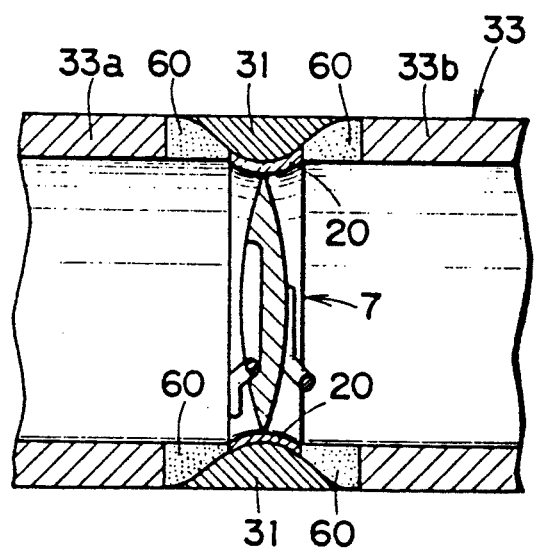
FIG. 11 is a cross-sectional view of a principal part of still another connector of the invention for the blood pumping device.
Figure 12:
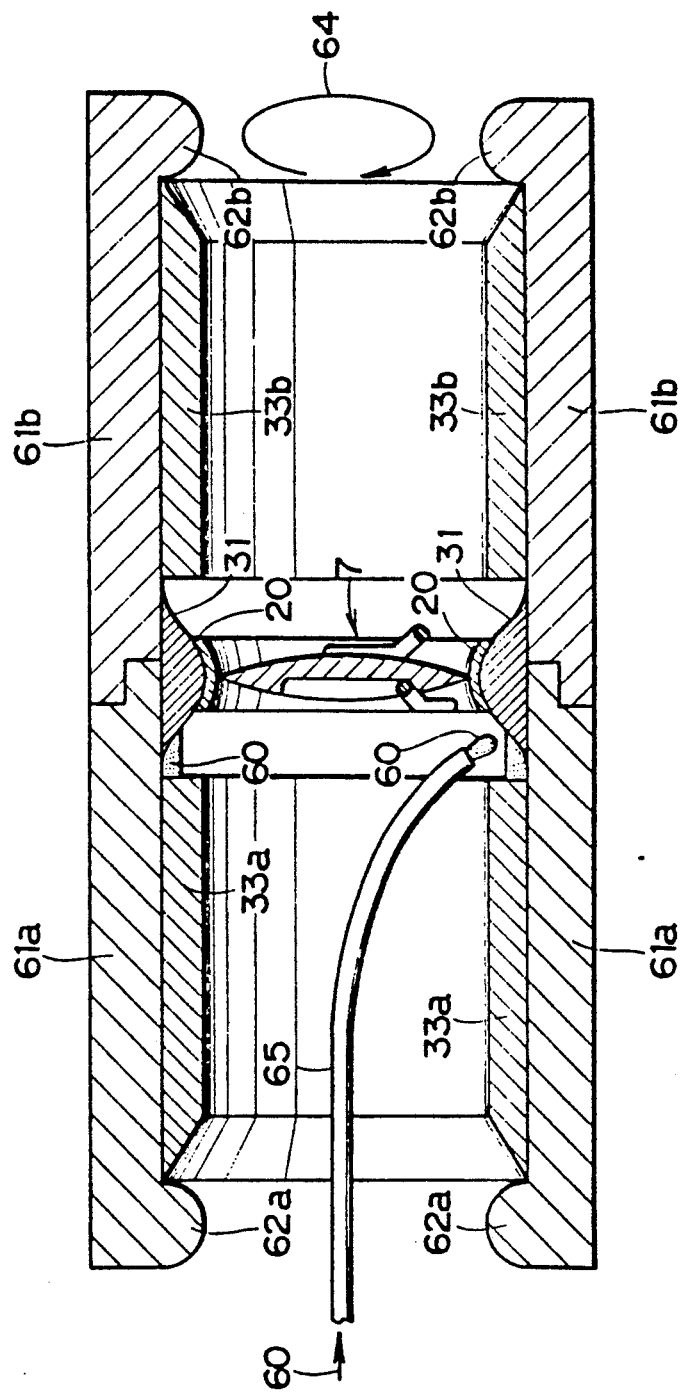
FIG. 12 is a cross-sectional view of the same connector at an assembly step thereof.

Another example of a connector, illustrated in FIGS. 11 and 12, not only just accommodates a built-in artificial valve 7 in a connector 33 but is particularly devised in the valve fitting construction of the connector. Namely, between a pair of separately formed tubular sections 33a and 33b, for example, made of epoxy resin and comprising the tubular connector 33, an artificial valve 7 is securely bonded with adhesives 60, for example, made of epoxy resin in such a manner that these two tubular sections 33a and 33b are jointed liquidtight into an integral unit. The artificial valve 7 is secured between the two tubular sections 33a and 33b by injecting adhesives 60 after the valve is placed in position with a valve seat 20 fitted closely to the inwardly swollen surface of an annular resilient mount 31, for example, made of polyurethane. The above construction wherein an artificial valve is built in a connector by bonding the valve between the two tubular sections 33a and 33b results in the following noticeable functions and effects.

First, since the artificial valve 7 is securely bonded between the two tubular sections 33a and 33b by injecting adhesives, even if the inner diameter or internal dimensions are not controlled so severely in the production process, the artificial valve 7 can always be bonded in a desirable direction and at a desirable position as long as the size of shell molds as mentioned later, height of mount 31, etc. are selected properly. Accordingly, unlike the conventional construction with an artificial valve built in the blood port, the present construction has wider allowances on sizes and dimensions, so that artificial valves of various shapes and sizes can be secured at a desirable position since variations, if any, in dimensions of individual parts involved are absorbed effectively.

Further, since the artificial valve 7 is bonded by injection of adhesives 60, the valve seat 20 can partially be embedded in the mass of adhesives to present a smoother surface (with less steps and gaps) to blood flow resulting in a reduction in thrombus formation. By contrast, the conventional blood pumping device as illustrated in FIG. 3 wherein a valve seat is fitted to a swelling in the inside surface of ports 3 and 4 is liable to formation of a step 21. With such a step 21, particularly when the artificial heart system is run at a low flow rate (for example, shortly before the assist part is removed in clinical cases), microthrombi will easily form and adhere to the wall defining the blood path both upstream and downstream of the valve seat 20.

To assemble the connector of this example, tubular sections 33a and 33b are disposed, as illustrated in FIG. 12, inside a pair of shell molds 61a and 61b that are linked to each other while a resilient artificial valve mount 31 to which a valve seat 20 of artificial valve 7 is closely fitted beforehand is placed in the inner surface of linked shell molds at the joint line thereof. The whole assembly is now turned in a circumferential direction as illustrated by an arrow 64, for example, at a rate of several thousands turns per minute while injecting a given amount of epoxy resin 60 from a syringe 65 that is inserted inside. As the shell molds 61a and 61b turn, therefore, resin is injected and distributed uniformly in an annular form between tubular section 33a and mount 31. Before the above resin injection process, however, it is advisable to lock the moving part, namely, occluder of artificial valve 7 by a proper means lest the part move to open and close. Resin 60 must also be injected on the other side of valve 7. This can be achieved by use of a resilient mount 31 that has such a configuration that resin may penetrate from one side to the other (for example, opening throughholes across the mount 31). Alternatively, a syringe as mentioned above may also be inserted from the other side to effect injection separately from the above one side.

It will be evident that various modifications can be made to the described embodiments without departing from the scope of the present invention.

For example, the configuration of the sealing construction at the junction of two tubular sections and in the artificial valve fixing area, artificial valve fixing design, materials of individual parts of the connector, etc. may be variously changed or modified. Further, the method of jointing the two tubular sections is not limited to screwing or bonding. For example, a clicking system for concavo-convex fitting may be applicable. It is noted that the artificial valve may be mounted in position not before the two tubular sections are jointed by screwing but after such screwing. For example, in FIG. 5, soft and hard tubes may be used for the tubular sections 33a and 33b, respectively, so that the tubular section 33a may accommodate the artificial valve as the valve is pushed in to widen the opening of this tubular section. In this case, however, it is advisable to wind and tighten a band around the outer circumference for fastening after valve installation. In the example of FIG. 9, the built-in probe may be made in various construction and mounted at a different position, for example, on the tubular section 33a. Further, it is noted that naturally the present invention also covers blood pumping devices other than the sac type, such as those of tubular type and diaphragm type. The pumping device of the invention is applicable for purposes other than an artificial heart, for example, as artificial lungs. The artificial valves may be replaced by another valve including a natural valve.

What is claimed is:

1. A tubular connector to connect first and second fluid tubes especially configured for a blood pumping device, said tubular connector comprising:
    an annular packing;
    a first formed single wall tubular section having a first end with an annular recess and a second end, said first end having a threaded portion formed on a circumference;
    a second formed single wall tubular section having a first end which is to be abutted with said first tubular wall section with said annular packing fitting between abutting faces thereof, said first end of said second tubular section having a threaded portion formed on a circumference extending from said first end to a shoulder, said second tubular section having a second end, one of said first and second tubular sections having the second end thereof connected to said blood pumping device and another tubular section having said second end thereof connected to a blood passage;
    a sealing ring fitted inside said annular recess of said first tubular section;
    a valve to control flow of fluid in an inside fluid path of said tubular connector, said valve having a valve seat fitted inside said sealing ring; and
    a union nut meshing said threaded portion of first tubular section toward said second tubular section until a rear end of the union nut is stopped by said shoulder, wherein said first and second tubular sections are firmly pressed together.

2. A tubular connector as claimed in claim 1 wherein said first and second tubular sections are detachably joined by said union nut.

3. A tubular connector as claimed in claim 2, wherein said first and second tubular sections are joined by screwing said union nut.

4. A tubular connector to connect first and second fluid tubes configured for a blood pumping device, said tubular connector comprising:
    a valve to control flow of fluid;
    a first formed single wall hollow tubular section having a first end with an end face and a second end and having a hollow center as an inside fluid path;
    a second formed single wall hollow tubular section having a hollow center as an inside fluid path and having a first end with an end face which is to be abutted with said first end of said first tubular wall section, said valve fitting between said abutting first ends and b) fitting inside said fluid paths of said first and second tubular sections, said second tubular section having a second end;
    a sealing ring fitted around said valve and between abutting first end faces of said first and second tubular sections; and
    an adhesive, joining said sealing ring and said first and second hollow tubular sections tightly.

5. A tubular connector as claimed in claim 4 wherein said valve is secured by said adhesive.

* * * * *